United States Patent
Babcock et al.

[11] 4,039,501
[45] Aug. 2, 1977

[54] PLASTICIZED HYDROPHILIC POLYMERS

[75] Inventors: Thomas E. Babcock, Mercer; Karel Kliment, Princeton; Richard F. Stockel, Somerville, all of N.J.

[73] Assignee: National Patent Development Corporation, New York, N.Y.

[21] Appl. No.: 582,333

[22] Filed: May 30, 1975

[51] Int. Cl.$^2$ .......................... C08K 5/06; C08K 5/15; C08K 5/16; C08K 5/20
[52] U.S. Cl. ............... 260/30.4 R; 260/32.4; 260/32.6 R; 260/33.2 R; 260/33.4 R; 260/33.8 UA
[58] Field of Search ............ 260/86.1 E, 32.4, 30.4 R, 260/33.2 R, 32.6 R, 33.4 R, 33.8 UA

[56] References Cited
U.S. PATENT DOCUMENTS

| | | | |
|---|---|---|---|
| 3,575,946 | 4/1971 | Chromecek et al. | 260/86.1 E |
| 3,597,384 | 8/1971 | Kugler et al. | 260/33.2 R |
| 3,607,848 | 9/1971 | Stoy et al. | 260/86.1 E |
| 3,784,540 | 1/1974 | Kliment et al. | 260/33.2 R |

Primary Examiner—Allan Lieberman
Attorney, Agent, or Firm—Cushman, Darby & Cushman

[57] ABSTRACT

Plasticized solid, water-insoluble, water-swellable, hydrophilic polymers having the recurring unit

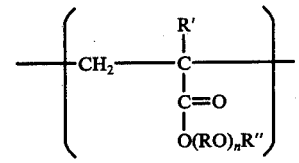

wherein R is a divalent aliphatic hydrocarbon radical of 2 to 8 carbon atoms; where R' is hydrogen or alkyl of 1 to 4 carbon atoms; preferably hydrogen or methyl; wherein R" is hydrogen or alkyl of 1 to 12 carbon atoms; and wherein n is an integer of at least 1; and as the plasticizer therefor, preferably a liquid compound characterized by amino and hydroxyl groups, said compound having a relatively low vapor pressure.

24 Claims, No Drawings

PLASTICIZED HYDROPHILIC POLYMERS

Polymers of hydroxyethyl methacrylate are finding more and more applications both in consumer products field and in cosmetics as coatings. Desirably, these coatings should either protect the substrate or impart some special properties to it. Examples are antibacterial coatings, coatings with slow release properties, and protective and moisturizing coatings in cosmetics.

Owing to the high $T_g$, i.e., glass transition temperature, of 2-hydroxyethyl methacrylate homopolymer, which is brittle in the dry state at room temperature, it is not suitable as a coating on soft or plastic substrates. This brittle characteristic of said polymer results in cracking of the coating and its subsequent peeling from the substrate.

Attempts to overcome this problem have been made in two ways. Internal plasticizing of the polymer can be achieved by chemically building into the polymeric structure other units which will impart a lower $T_g$ value to the resulting polymer. For example, long-chain acrylates and methacrylates, e.g., butyl acrylate or stearyl methacrylate, can be copolymerized with 2-hydroxyethyl methacrylate to yield polymeric products which give films having good mechanical properties in the dry state at room temperature and which can be safely used on soft surfaces. However, such long-chain comonomers are invariably hydrophobic and consequently, the copolymer product exhibits lower hydrophilic properties, lower swelling in water, lower diffusion rates, etc., than the homopolymer. This sometimes is contrary to the original reason why a hydrophilic polymer was used in the first place and renders these copolymers impractical.

A second possibility is the use of external plasticizers. These must be high-boiling organic vehicles, which must be good solvents (or co-solvents) for the polymer, so that they can be incorporated readily into its solutions, preferably with low toxicity, no smell and color of their own, and be readily available. When a polymeric film is cast from a solution of a solvent and plasticizer, the solvent evaporates, leaving a film of the polymer, which is still partially dissolved or at least swelled in the plasticizer. As the plasticizer has a high boiling point, it stays in the film for a long time, preferably for the life of the film.

It is known that for hydroxyethyl methacrylate polymer external plasticizers include the glycols, e.g., ethylene glycol and propylene glycol, glycerol, and glycerol diacetate. All of these are high boiling, are solvents for the polymer and can be easily incorporated into its solutions. Nevertheless, they have two significant disadvantages: (1) they do evaporate slowly such that the plasticizing effect diminishes with time, and (2) they are easily washed out with water. Oftentimes one short water immersion of the plasticized film is enough to remove most of the plasticizer and completely offset its influence on the mechanical properties of the film.

Other high molecular weight compounds have been tested by applicants as plasticizers for hydroxyethyl methacrylate polymers. Such plasticizers include polyethylene glycol-lanolin condensate, various low molecular weight polyethylene glycols (mol. wt. of 400–1000), sorbitol, lanolin, silicone oils, as well as some standard plasticizers like diethyl phthalate, acetyltriethyl citrate, etc. Most of these compounds work to some degree as plasticizers, but many problems were encountered with them. Several of then do not give smooth, non-tacky films, are odoriferous, and/or are toxic.

It has been found that excellent plasticizers for polymers of 2-hydroxyethyl methacrylate and various other polymers as disclosed hereinafter are compounds having an amino group and a hydroxyl group in the molecule, that is, aminohydroxy compounds, desirably aminoalcohols which are preferably liquid at room temperature. These compounds have been widely used in the coating and plastic industries as additives which improve adhesion, durability, flexibility and impact resistance. They are high boiling, e.g., between 165° and 345° C., with low vapor pressure, have no strong odor or color, and their toxicity is low. However, they have not been proposed for use with hydroxyethyl methacrylate polymers or the like.

Polymers of 2-hydroxyethyl methacrylate are characterized by a recurring unit which contains two polar groups

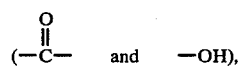

the former being the donor or proton, the latter both the donor and the acceptor of proton. Therefore, one-component good solvents for such polymers have to be looked for among strongly polar liquids possessing an outstanding capacity of providing either electrons or protons. The aminohydroxy compounds fulfill this condition. Besides, they are capable of hydrogen bonding with the 2-hydroxyethyl methacrylate unit in solutions both by the —OH and —NH$_2$ groups. It is probable that this last property explains why they are not so easily washed out of the polymeric films as the polyhydroxy compounds, e.g., glycol.

The use of aminohydroxy compounds as plasticizers for hydroxyethyl methacrylate polymers and other polymers has several advantages:

1. The aminohydroxy compounds are good solvents for such polymers. With water, e.g., 1:1 weight ratio, they form a cosolvent mixture. They are fully compatible with the solvents conventionally used for the polymers, e.g., alcohols such as ethanol and isopropanols; methoxyalcohols, e.g., methoxyethanol; and various co-solvent mixtures.

2. As opposed to polyhydroxy compounds, the aminohydroxy compounds actually improve the propellant compatibility of the hydroxyethyl methacrylate polymer solutions, e.g., with fluorinated carbon compound propellants.

3. They give non-tacky films even in relatively higher concentrations.

4. They are relatively high boiling and have low vapor pressures, e.g., below 2 mm at room temperature so that they do not evaporate from the polymeric films.

5. They have low odor, are virtually colorless, and have low toxicity.

6. They improve the adhesion, gloss, mar resistance, flexibility and impact resistance of the polymeric films.

7. As opposed to the polyhydroxy compounds, they resist washing out by water, the films remain plasticized even after being soaked in water.

The novel hydrophilic polymer preparations preferably comprise:

a. A hydrophilic polymer characterized by the recurring unit hereinafter described in detail. The methanolsoluble hydrophilic polymers can be prepared according to the teachings of U.S. Pat. No. 3,575,946 (to Chromecek) or U.S. Pat. No. 3,784,540 (to Kliment). On the other hand, the methanol-insoluble polymers can be prepared according to the teaching of U.S. Pat. No. 2,976,576 and 3,220,960. The entire disclosures of the aforesaid patents are hereby incorporated by reference and relied upon.

b. A plasticizer for said polymer which is preferably a normally-liquid aminohydroxy compound, i.e., a compound which has at least one —OH group and at least one —$NH_2$ or —NHR, or —$NR_2$ group in the molecule.

c. A third component which is an inert, normally-liquid organic vehicle or diluent in which the hydrophilic polymer is soluble and which vehicle is also miscible with the plasticizer. Suitable vehicles includes the organic solvents disclosed or characterized in U.S. Pat. No. 3,575,940 (to Chromacek) as a good solvent for the hydrophilic polymer.

The novel plasticized hydrophilic polymers, depending on their end-use, can contain conventional ingredients such as bacteriacidal agents, e.g., bacitracin or tetracycline or sulfanilamide; flavoring agents, e.g., lemon oil; fragrances, e.g., attar of roses; humectants, e.g., glycerol; emmolients, e.g., lanolin; dyes; propellants; etc., which ingredients have to be chosen in such a manner that they would be compatible with the two and generally three basic components and will not impair their performance in the polymeric film.

Examples of propellants which can be employed include fluorine-containing halocarbons such as dichlorodifluoromethane, trichlorofluoromethane, dichlorodifluoroethane, difluoroethane, chlorodifluoroethane, dichlorotetrafluoroethane.

The aminohydroxy plasticizer is used in an amount which is sufficient to impart improved properties to the resulting plasticized polymer, i.e., improvement in flexibility, lowering of $T_g$, etc. In general, the plasticizer can be used in an amount of from 1 to 100 parts, preferably 5 to 50 parts, per 100 parts of polymer by weight.

The amount of organic diluent which is employed in the practice of desirable embodiments of the invention can vary widely, e.g., 30 to 95% of solvent based on the weight of the total composition. The solvent is normally not present in the final plasticized product.

The solid, water-insoluble, water-swellable, hydrophilic polymers have the recurring unit

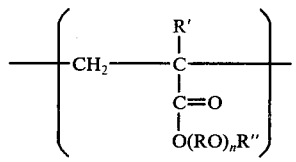

wherein R is a divalent aliphatic hydrocarbon radical of 2 to 8 carbon atoms, preferably alkylene of 2 to 4 carbon atoms, and more preferably still ethylene; wherein R' is hydrogen or alkyl of 1 to 4 carbon atoms, preferably methyl; wherein R" is hydrogen or alkyl of 1 to 12 carbon atoms, preferably hydrogen or alkyl of 1 to 4, and more preferably hydrogen; and wherein $n$ is an integer of at least 1, e.g., 1 to 6, preferably one. A preferred class of hydrophilic polymers are those which are characterized by at least about 50 weight percent, and most preferably by at least about 75 weight percent, of the recurring unit noted above. Hydrophilic polymers which are methanolsoluble are preferred. A wide variety of comonomers can be chemically combined in the hydrophilic polymer. When R" is other than hydrogen there should be present sufficient hydrophilic groups in the polymer molecule to make the overall polymer hydrophilic. The hydrophilic polymers which are suitable include those whose average molecular weights range from 20,000 to 5,000,000 desirably from 40,000 to 1,000,000 and preferably from 50,000 to 1,000,000. The water-swellability should be between 10 and 100%, preferably 20 to 75%.

Preferably the hydrophilic monomer used to prepare the hydrophilic polymer is hydroxyalkyl monoacrylate or a hydroxyalkyl monomethacrylate, such as 2-hydroxyethyl acrylate, 2-hydroxyethyl methacrylate, diethylene glycol monoacrylate, diethylene glycol monomethacrylate, hydroxypropyl acrylate, hydroxypropyl methacrylate, tetraethylene glycol monomethacrylate, pentaethylene glycol monomethacrylate, dipropylene glycol monomethacrylate, dipropylene glycol monoacrylate, and similar hydrophilic monomers. The most preferred monomer is 2-hydroxyethyl methacrylate and the next most preferred monomer is 2-hydroxyethyl acrylate. Additionally there can be used as the monomer hexaethylene glycol monoacrylate, hexaethylene glycol methacrylate, octaethylene glycol acrylate, octaethylene glycol methacrylate, 4-hydroxybutyl methacrylate, methoxyethyl acrylate, methoxyethyl methacrylate, ethoxyethyl acrylate, ethoxyethyl methacrylate, methoxypropyl acrylate, methoxypropyl methacrylate, methoxyethoxyethyl acrylate, methoxyethoxyethyl methacrylate, butoxyethyl acrylate, butoxyethyl methacrylate, dodecoxyethyl acrylate, dodecoxyethyl methacrylate, propoxyethyl acrylate, propoxyethyl methacrylate, and the like.

The term "copolymers," as used herein, is employed in its generic sense to cover polymers of 2, 3, 4 or more monomers chemically combined therein. Such copolymers include copolymers of the hydroxyalkyl monoacrylates or of the hydroxyalkyl monomethacrylates illustrated above, with 1 to 50 percent, preferably 5 to 25 percent, of alkyl acrylates and alkyl methacrylates such as methyl acrylate, ethyl acrylate, the propyl acrylates, e.g., propyl acrylate and isopropyl acrylate, the butyl acrylates, e.g., n-butyl acrylate, methyl methacrylate, ethyl methacrylate, the propyl methacrylates, the butyl methacrylates, e.g., n-butyl methacrylate, and the higher alkyl acrylates and higher alkyl methacrylates having up to 18 carbon atoms, for example, lauryl acrylate, lauryl methacrylate, stearyl acrylate, stearyl methacrylate, and 2-ethylhexyl acrylate.

Suitable copolymers include copolymers of the hydroxyalkyl acrylates or the hydroxyalkyl methacrylates illustrated above, with 1 to 60 percent, preferably 5 to 25 percent, of the alkoxyalkyl acrylates and alkoxyalkyl methacrylates where the alkyl moiety has at least 2 carbon atoms, preferably 2 to 4 carbon atoms, and the alkoxy moiety has 1 to 18 carbon atoms, usually 1 to 4 carbon atoms, such as methoxyethyl acrylate, ethoxyethyl acrylate, propoxyethyl acrylate, butoxyethyl acrylate, methoxypropyl acrylate, methoxybutyl acrylate, methoxyethyl methacrylate, ethoxyethyl methacrylate, propoxyethyl methacrylate, butoxyethyl methacrylate, ethoxypropyl methacrylate, and higher alkoxyalkyl acrylates and higher alkoxyalkyl methacrylates, e.g., octoxyethyl acrylate and stearoxyethyl methacrylate.

There can also be employed copolymers of the hydroxyalkyl acrylates and the hydroxyalkyl methacrylates illustrated above with 0.1 to 25 percent, usually at least 1 percent and preferably 5 to 15 percent, of ethylenically unsaturated amines or amides. Preferably there can be used the alkylaminoalkyl acrylates and alkylaminoalkyl methacrylates, the vinylpyridines and alkylvinylpyridines, the dialkylaminoalkyl vinyl esters, the acrylamides or the methacrylamides, e.g., N-alkylarylamides or N,N-dialkylacrylamides, N-alkyl methacrylamides or N,N-dialkyl methacrylamides, the vinylpyrrolidones, and other ethylenically unsaturated amines and amides, e.g., aminoethyl methacrylate, dimethylaminoethyl methacrylate, monomethylaminoethyl methacrylate, p-aminostyrene, o-aminostyrene, 2-amino-4-vinyltoluene, diethylaminoethyl acrylate, dimethylaminoethyl acrylate, piperidinoethyl acrylate, piperidinoethyl methacrylate, morpholinoethyl methacrylate, 2-vinylpyridine, 3-vinylpyridine, 4-vinylpyridine, 2-ethyl-5-vinylpyridine, dimethylaminopropyl acrylate, dimethylaminopropyl methacrylate, dimethylaminoethyl vinyl ether, dimethylaminoethyl vinyl sulfide, diethylaminoethyl vinyl ether, aminoethyl vinyl ether, 2-pyrrolidinoethyl methacrylate, 2-aminoethyl methacrylate. N-vinylpyrrolidone, acrylamide, methacrylamide, N-methylacrylamide, N,N-dimethylacrylamide, N-methylmethacrylamide, N,N-dimethylmethacrylamide, N-isopropylacrylamide, N-isopropylmethacrylamide, N-ethylacrylamide, N-butylacrylamide, N-butylmethacrylamide, N-(2-hydroxyethyl)acrylamide and N-(2-hydroxyethyl)methacrylamide.

Furthermore, there can be employed copolymers of the hydroxyalkyl acrylates and of the hydroxyalkyl methacrylates illustrated above with 0.1 to 15 percent, usually at least 1 percent, and preferably 5 to 15 percent of ethylenically unsaturated carboxylic acids. These include acrylic acid, methacrylic acid, fumaric acid, itaconic acid, aconitic acid, cinnamic acid, crotonic acid, maleic acid, mono-2-hydroxyethyl itaconate, mono-2-hydroxypropyl citraconate, mono-2-hydroxyethyl maleate, and mono-2-hydroxypropyl fumarate.

There can also be used numerous other alkyl, alkoxyalkyl, sulfoalkyl, sulfoalkylamide, and dialkylaminoalkyl acrylates and/or methacrylates.

The hydrophilic polymers can be prepared from the polymerizable monomers, preferably in the absence of a solvent and in the presence of at least about 0.05% of a crosslinking agent, generally from about 0.1 to 5%, and preferably from about 0.2 to 2. Such polymers are considered to be cross-linked to varying degrees and methanol-insoluble. The crosslinking agent can favorably influence the mechanical properties and the swelling and chemical resistance of the hydrophilic polymer product. Illustrative crosslinking agents are the diacrylates and/or the dimethacrylates of ethylene glycol and its homologues, including mono-, di-, tri-, tetra and higher poly-, etc., ethyleneglycol. Illustrative crosslinking agents include ethylene glycol diacrylate, ethylene glycol dimethacrylate, 1,4-butylene dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate.

Methanol-soluble hydrophilic polymers can be prepared by maintaining the concentration of the crosslinking agent in the polymerizable mixture to extremely small amounts, e.g., less than 0.02%. Also, methanol-soluble polymers can be prepared by following the teachings disclosed in U.S. Pat. No. 3,575,946 (to Chromecek) and U.S. Pat. No. 3,784,540 (to Kliment).

In the practice of a desirable embodiment of the invention, the concentration of hydrophilic polymer in the organic solvent-containing formulation is from 0.1 weight percent to 20.0 weight percent, preferably between 0.5 weight percent and 5.0 weight percent, although the amount of polymer can be outside this range. The solvents used for these novel formulations include those specified in the U.S. Pat. No. 3,575,946 (to Chromecek). Naturally for certain consumer and cosmetic products the choice is limited to solvents with low toxicity such as ethanol, isopropanol, ethoxyethanol, and co-solvent mixtures (for example, acetone-water, ethanol-dichloromethane, etc.). The practical amount of solvent in the formulation is between 30 weight percent and 95 weight percent but there can even be 96 or 99.9 weight percent of solvent depending if the final formulation is a solution or an aerosol package.

The plasticizers which are suitable in the practice of the invention are characterized by at least one hydroxy (—OH) group, at least one amino group (primary, secondary and/or amino), and are composed of carbon, hydrogen, amino nitrogen, and oxygen atoms. The oxygen is preferably in the form of hydroxylic oxygen. Such plasticizers have a boiling point at 760 mm of Hg greater than 165° C and a vapor pressure of less than 5 mm of Hg, preferably less than 1 mm of Hg, under standard conditions (1 atmosphere at 22° C). Desirably, the plasticizers contain from 1 to 3 hydroxy groups and from 1 to 3 amino groups, and preferably from 2 to 10 carbon atoms. Such carbon atoms preferably are acyclic carbon atoms. Illustrative aminohydroxy compounds include:

2-amino-2-methyl-1-propanol,
2-amino-2-methyl-1,3-propanediol,
2-amino-2-ethyl-1,3-propanediol,
2-amino-1-butanol,
diisopropanolamine,
triethanolamine, and
diethanolamine.

Compounds such as polyoxethylene cocoamine and polyoxyethylene stearamine are suitable as well. The plasticizers are compatible with and inert to the hydrophilic polymer and, in preferred embodiments, having boiling points below 365° C.

The novel hydrophilic polymer formulations can be prepared by various routes. For example, conventional roll mill techniques can be used to intimately blend a mixture containing methanol-soluble hydrophilic polymer and plasticizer. Methanol-soluble polymer and plasticizer can be dissolved in a suitable solvent and the resulting solution then cast into a film. A solution containing methanol-soluble polymer and plasticizer can be prepared by polymerizing a mixture containing the appropriate polymerizable monomer and plasticizer in a suitable solvent and in the absence of a cross-linking agent (in reality, a very small amount of such agent is present as trace impurities).

In a further route, a mixture of polymerizable monomer, crosslinker, and plasticizer, preferably in the absence of a solvent, is subjected to polymerization conditions to thus obtain methanol-insoluble polymers plasticized with the plasticizer of choice.

The polymer type and amount, as well as the type and amount of the solvent depend on the end-use of the solution. There can be added to the formulation any desired additives for specific uses.

The composition of the invention can be used for coating purposes, e.g., to coat leather or vinyl polymers, e.g., polyvinyl choride, or in shoe polish formulations, as spray-on compositions, etc.

Unless otherwise indicated all parts and percentages are by weight.

EXAMPLE 1

A hydrophilic polymer formulation was prepared by dissolving 3 parts of poly(2-hydroxyethyl methacrylate) prepared according to U.S. Pat. No. 3,784,540 (to Kliment), (reduced viscosity of 0.5 gram of polymer in 100 ml of methoxyethanol at 25° C = 0.84) in 96 parts of isopropyl alcohol.

To the clear solution 1 part of 2-amino-2-methyl-1-propanol was added and a film was cast from the resulting solution on (a) polyethylene foil, (b) vinyl chloride polymer foil and (c) glass plate as substrates. After drying each film was clear and non-tacky. As a control, a film was cast on each of the substrates from a solution of the polymer in alcohol alone. The non-plasticized films cracked when bent, while the plasticized films remained supple and did not crack even after 2-week aging on air (25°, relative humidity 55–60%) or after 30 minute leaching in deionized water and subsequent drying.

EXAMPLE 2

Novel hydrophilic polymer formulations were prepared as in Example 1 from 3 parts of polymer, 96 parts isopropyl alcohol and 1 part 2-amino-2-methyl-1-propanol, but different polymers were used instead of poly(2-hydroxyethyl methacrylate). The polymer compositions were cast into films and tested in the same manner as the polymer composition of Example 1. In present Example 2 the polymers employed were as follows:

a. 90% 2-hydroxyethyl methacrylate — 10% methyl methacrylate
b. 80% 2-hydroxyethyl methacrylate — 20% methyl methacrylate
c. 90% 2-hydroxyethyl methacrylate — 10% methacrylic acid
d. 90% 2-hydroxylethyl methacrylate — 10% itaconic acid
e. 90% 2-hydroxyethyl methacrylate — 10% n-butyl methacrylate
f. 80% 2-hydroxyethyl methacrylate — 20% n-butyl methacrylate
g. 50% 2-hydroxyethyl methacrylate — 50% diethyleneglycol methacrylate
h. 60% 2-hydroxyethyl acrylate — 40% methyl methacrylate
i. 90% 2-hydroxyethyl methacrylate — 10% hydroxypropyl acrylate
j. 90% 2-hydroxyethyl methacrylate — 10% ethoxyethyl methacrylate
k. 90% 2-hydroxyethyl methacrylate — 10% dimethylaminoethyl methacrylate The films were similar in properties to those of Example 1.

EXAMPLE 3

Novel hydrophilic polymer formulations were prepared and cast into films as in Example 1, but the following solvents or co-solvent mixtures were used instead of isopropyl alcohol and in the same amount of total solvent. Such solvents are compatible with and inert to the major components of the novel formulation, i.e., hydrophilic polymer and plasticizer:

methanol, ethanol, isopropanol, sec-butanol, t-butanol, cyclohexanol, cyclopentanol, tetrahydrofuran, 2,2-dimethyl-propanol, 2-methyl-2-butanol, 3-pentanol, 2-methoxyethanol, 2-ethoxyethanol, diacetone alcohol, dimethylformamide, dimethylsulfoxide, pyridine, benzyl alcohol, 50 acetone/50 water, 50 dioxane/50 water, 80 methoxyethanol/20 water, 60 ethanol/40 water, 50 ethanol/50 dichloromethane, 80 ethanol/20 chloroform, 60 ethanol/40 1,1-dichloroethylene, and 50 ethanol/50 trichloroethylene.

Desirable subclasses of solvents can be illustrated by aliphatic alcohols (which term includes cycloaliphatic alcohols), cyclic ethers, dialkyl ethers, and alkanamides.

The films prepared had similar properties to the products of Example 1.

EXAMPLE 4

Novel hydrophilic polymer formulations were prepared and cast into films as in Example 1, but the same amount of each of the following compounds were used as plasticizers in place of the aminomethyl-propanol.

a. 2-amino-1-butanol
b. 2-amino-2-methyl-1,3-propanediol
c. 2-amino-2-ethyl-1,3-propanediol
d. diisopropanolamine
e. triethanolamine
f. diethanolamine
g. polyoxyethylene cocoamine (Ethomeen C-25 - Armek Chemical Division of Okzona, Inc.)

The films had similar properties to the products of Example 1.

EXAMPLE 5

A non-cracking high glaze, water resistant shoe polish was prepared using the following formulation:

| | |
|---|---|
| copolymer of 80 parts 2-hydroxyethyl methacrylate and 20 parts n-butyl methacrylate* | 4 parts |
| 2-amino-2-methylpropanol (plasticizer) | 1 part |
| Silicone L 7604**(Union Carbide) | 0.5 part |
| isopropyl alcohol | 69.5 parts |
| dichlorodifluoromethane (propellant) | 25 parts |

*Reduced viscosity value of 0.75. Measured at concentration of 0.5 gm of polymer in 100 ml. of methoxyethanol at 25°C.
**Silicone - oxyalkylene block copolymer - leveling agent The hydroxyethyl methacrylate-butyl methacrylate copolymer was dissolved in the alcohol, then the plasticizer and the silicone were added. The resulting mixture was filled into aerosol cans, the cans capped, and the propellant filled through the valve.

This composition when sprayed on both leather and plastic shoes, i.e., the uppers of the shoes, gives a high gloss finish, which dries to a smooth, non-tacky film in under 5 minutes. The film is scuff resistant, water resistant and does not crack even after prolonged wearing (over two weeks).

EXAMPLE 6

A vinyl chloride polymer top protective coating for car tops was prepared using a formula like that in Example 5, except the polymer used was the poly(2-hydroxyethyl methacrylate) of Example 1 and the silicone used was Silicone Y 502] (silicone-oxyalkylene block copolymer-leveling agent, Union Carbide).

Instead of the dichlorodifluoromethane in this example different propellents can be used, e.g.,
a. difluorochloromethane
b. difluoroethane
c. trichlorofluoromethane
d. chlorodifluoroethane and their mixtures.

The coating had excellent weather and UV (ultraviolet light) resistance and exhibited soil-release properties.

EXAMPLE 7

A shoe polish (Example 5) or "Vinyl Top" protective coating (Example 6) can be modified by addition of dyes or pigments. For example, the following were tested in each formulation:

| | |
|---|---|
| (a) Carbon Black (A3278 - H. Kohnstamm) | 2 parts added to the formulation |
| (b) Titanium Dioxide (Whittaker, Clark & Daniels) | 2 parts added to the formulation |
| (c) FD&C Blue #1 (Aluminum Lake) | 0.2 parts added to the formulation |

EXAMPLE 8

A shoe polish (Example 5) or "Vinyl Top" protective coating (Example 6) can be modified by addition of fragrances, which are slowly released from the coating. For example, the following were tested:

| | |
|---|---|
| Leather Musk (#323 Felton) | 0.2–2 parts added to the formulation |
| New Car Fragrance (#706, Felton) | 0.2–2 parts added to the formulation |

EXAMPLE 9

The novel hydrophilic polymer formulations prepared according to Examples 1, 2, 3 and 4 are suitable as protective and/or decorative coatings for masonry, stone, wood, vinyl polymers, e.g., polyvinyl chloride, rubber and even cloth. They can be modified by addition of waxes, emmolients or humectants, and can have incorporated therein fragrances, dyes or pigments or even bactericidal agents.

Matting agents or anti-static additives can also be added to achieve special effects.

The novel compositions can comprise, consist of or consist essentially of the indicated materials.

It will be observed that in the Examples the aminohydroxy plasticizers were aminoalkanols, more specifically aminoalkanols having 2 to 10 carbon atoms and still more specifically aminoalkanols having one amino group and 1 to 3 alcohol groups. The amino group or groups in the plasticizer can be primary, secondary or tertiary.

The solvents can be any of these mentioned in Examples 1 and 3, for example and preferably include a lower alkanol, e.g., containing 1 to 4 carbon atoms. Ketones can be used such as acetone, methyl ethyl ketone and diacetone alcohol (a compound having both an alcohol and a ketone group).

The hydrophilic polymers are soluble in organic solvents; in various cases, they are soluble in mixed water-organic solvents, e.g., water-lower alkanol or water-water soluble ketone mixtures as well as dioxane-water mixtures.

What is claimed is:

1. A plasticized polymer composition comprising (1) a solid, water-insoluble, water-swellable hydrophilic polymer having the recurring unit

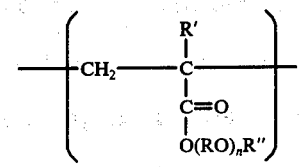

wherein R is a divalent aliphatic hydrocarbon radical of 2 to 8 carbon atoms, R' is hydrogen or alkyl of 1 to 4 carbon atoms, R'' is hydrogen or alkyl of 1 to 12 carbon atoms, and $n$ is an integer of at least 1; and (2) as the plasticizer therefor, an aminoalcohol composed of carbon, hydrogen, amino nitrogen, and oxygen atoms, said aminoalcohol having a boiling point at 760 mm of Hg greater than 165° C., a vapor pressure of less than 5 mm of Hg under standard conditions, from 1 to 3 hydroxy groups, and from 1 to 3 amino groups, the plasticizer being present in an amount of 1 to 100 weight percent of the weight of the polymer.

2. The composition of claim 1 wherein said aminoalcohol is an acyclic compound.

3. The composition of claim 2 including (3) an inert organic vehicle which is a solvent for the polymer and which is miscible with the plasticizer, the concentration of said polymer being from 0.1 to 20 weight percent of the composition, the concentration of said solvent being from 30 to 95 weight percent of the composition, and the concentration of said plasticizer being from 1 to 100 weight percent of the weight of said polymer.

4. The composition of claim 3 wherein said vehicle comprises an aliphatic alcohol, cyclic ethers, dialkyl ethers, and alkanamides as a volatile solvent.

5. The composition of claim 2 wherein R has 2 to 3 carbon atoms, R' is hydrogen or methyl, and R'' is hydrogen or alkyl of 1 to 4 carbon atoms and $n$ is 1 to 6.

6. The composition of claim 5 wherein R is ethylene, R' is methyl, R'' is hydrogen, and $n$ is 1.

7. The composition of claim 6 wherein at least 50 weight percent of the polymer is made of said recurring unit.

8. The composition of claim 6 wherein at least 75 weight percent of the polymer is made of said recurring unit.

9. The composition of claim 8 wherein the aminoalkanol has 2 to 10 carbon atoms.

10. The composition of claim 8 including (3) an inert, volatile liquid organic vehicle which is a solvent for polymer and which is miscible with the plasticizer.

11. The composition of claim 10 including (4) a propellant.

12. The composition according to claim 3 wherein the aminoalkanol boils at 165° to 345° C.

13. The composition of claim 12 wherein the polymer is a polymer of 2-hydroxyethyl methacrylate.

14. A film made of the composition of claim 2.

15. The composition of claim 3 wherein the hydrophilic polymer is either a homopolymer having said recurring units or a copolymer of a monomer having the formula

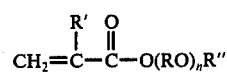

with
a. 1 to 50% of an alkyl acrylate or alkyl methacrylate,
b. 1 to 60% of an alkoxyalkyl acrylate or alkoxyalkyl methacrylate wherein the alkoxy moiety has 1 to 18 carbon atoms and the alkyl moiety has 2 to 4 carbon atoms,
c. 0.1 to 25% of an ethylenically unsaturated amine or amide
d. 0.1 to 15% of an ethylenically unsaturated carboxylic acid, or
e. a copolymer containing at least 0.05% of a cross-linking agent.

16. The composition according to claim 15 wherein the polymer is free of crosslinking agent.

17. The composition according to claim 15 wherein the polymer is cross-linked by at least 0.5% of a cross-linking agent.

18. The composition of claim 15 wherein the polymer has a molecular weight of 20,000 to 5,000,000 and a water swellability between 10 and 100%.

19. The composition of claim 1 wherein the polymer has at least 50% of said recurring units.

20. The composition of claim 19 wherein the polymer has at least 75% of said recurring units.

21. The composition of claim 1 wherein the hydrophilic polymer is either a homopolymer having said recurring units or a copolymer of a monomer having the formula

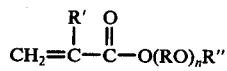

with
(a) 1 to 50% of an alkyl acrylate or alkyl methacrylate, (b) 1 to 60% of an alkoxyalkyl acrylate or alkoxyalkyl methacrylate wherein the alkoxy moiety has 1 to 18 carbon atoms and the alkyl moiety has 2 to 4 carbon atoms, (c) 0.1 to 25% of an ethylenically unsaturated amine or amide, (d) 0.1 to 15% of an ethylenically unsaturated carboxylic acid, or (e) a copolymer containing at least 0.05% of a crosslinking agent.

22. The composition of claim 21 wherein the polymer has a molecular weight of 20,000 to 5,000,000.

23. The composition of claim 22 wherein the polymer has a water swellability between 10 and 100%.

24. The composition of claim 23 wherein the polymer is a polymer of 2-hydroxyethyl methacrylate.

* * * * *